United States Patent [19]
Taoda et al.

[11] Patent Number: 5,650,126
[45] Date of Patent: Jul. 22, 1997

[54] DEODORIZING LAMP AND METHOD FOR PRODUCTION THEREOF

[75] Inventors: Hiroshi Taoda, Nagoya; Eiji Watanabe, Aichi-ken, both of Japan

[73] Assignee: Agency of Industrial Science & Technology, Ministry of International Trade & Industry, Tokyo, Japan

[21] Appl. No.: 533,137

[22] Filed: Sep. 25, 1995

Related U.S. Application Data

[63] Continuation of Ser. No. 215,627, Mar. 22, 1994, abandoned.

[30] Foreign Application Priority Data

Apr. 19, 1993 [JP] Japan ..................... 5-115439

[51] Int. Cl.$^6$ ........................................ A61L 9/20
[52] U.S. Cl. ..................... 422/122; 422/5; 422/121; 502/325
[58] Field of Search ................ 422/4, 5, 120–122; 502/325, 339, 350, 344–345, 347

[56] References Cited

U.S. PATENT DOCUMENTS

| | | | |
|---|---|---|---|
| 2,774,903 | 12/1956 | Burns | 313/109 |
| 3,141,990 | 7/1964 | Ray . | |
| 3,377,494 | 4/1968 | Repsher . | |
| 3,930,796 | 1/1976 | Haensel | 422/122 |
| 4,088,802 | 5/1978 | Shriver, Jr. . | |
| 4,308,186 | 12/1981 | Schreurs . | |
| 4,336,479 | 6/1982 | Kodama et al. | 313/487 |
| 4,361,598 | 11/1982 | Yoldas . | |
| 4,955,208 | 9/1990 | Kawashima et al. | 62/264 |
| 4,998,038 | 3/1991 | Watanabe et al. . | |
| 5,045,288 | 9/1991 | Raupp et al. | 422/186.3 |
| 5,051,650 | 9/1991 | Taya et al. | 313/112 |
| 5,082,820 | 1/1992 | Mitsui et al. | 502/350 |
| 5,157,007 | 10/1992 | Domesle et al. | 502/325 X |
| 5,187,415 | 2/1993 | Osawa et al. | 313/326 |
| 5,227,693 | 7/1993 | Sakakibara et al. | 313/489 |
| 5,291,742 | 3/1994 | Kawatani et al. | 422/125 X |
| 5,403,513 | 4/1995 | Sato et al. . | |

FOREIGN PATENT DOCUMENTS

| | | |
|---|---|---|
| 36 36 676 | 5/1987 | Germany . |
| 61-151739 | 9/1986 | Japan . |
| 1-159030 | 6/1989 | Japan . |
| 1-159033 | 6/1989 | Japan . |
| 2-207824 | 8/1990 | Japan . |
| 5-115439 | 1/1996 | Japan . |

OTHER PUBLICATIONS

Patent Abstracts of Japan, vol. 16, No. 556 (C–1007) (5599), Nov. 26, 1992, JP–4–215841, Aug. 6,1992 (with U.S. 5,252, 190).

Ullmann's Encyclopedia of Industrial Chemistry, vol. A 20, 1992, pp. 271–272, 288–290, 520.

"Industrial Materials", vol. 41, No. 1, p. 10. 1993.

*Primary Examiner*—Timothy McMahon
*Assistant Examiner*—Leigh Dawson
*Attorney, Agent, or Firm*—Oblon, Spivak, McClelland, Maier & Neustadt, P.C.

[57] ABSTRACT

A deodorizing lamp comprises a lamp unit and a titanium oxide film coating the glass surface of the lamp unit and optionally at least one metal selected from among iron, platinum, rhodium, ruthenium, palladium, silver, copper, zinc, and manganese deposited on the surface of the titanium oxide film. A method for the production of a deodorizing lamp comprises the steps of applying a titania sol or an aqueous hydrogen peroxide solution of titania gel to the glass surface of a lamp unit, drying the applied layer of titania sol or titania gel, firing the dried layer thereby forming a titanium oxide film on the glass surface, and optionally depositing at least one metal from among iron, platinum, rhodium, ruthenium, palladium, silver, copper, zinc, and manganese on the titanium oxide film.

19 Claims, No Drawings

DEODORIZING LAMP AND METHOD FOR PRODUCTION THEREOF

This application is a continuation of application Ser. No. 08/215,627, filed on Mar. 22, 1994, now abandoned.

BACKGROUND OF THE INVENTION

1. Field of the Invention

This invention relates to a deodorizing lamp and a method for the production thereof. More particularly, this invention relates to a deodorizing lamp which cleans air by decomposing malodorous substances in the air, operates safely, and retains its ability to decompose malodorous substances for a long time, and a method for the production of the deodorizing lamp.

2. Description of the Prior Art

When a semiconductor is exposed to light, it produces electrons that exert a strong reducing action and positive holes that exert a strong oxidizing action. It thus decomposes compounds which happen to come in contact with it by oxidation and reduction. This photocatalytic action of the semiconductor can be harnessed for easily decomposing and removing malodorous substances in the air. One example of a device utilizing the photocatalytic action of a semiconductor for removing malodorous substances by decomposition consists of a fluorescent lamp having a cover lined with a semiconductor ["Industrial Materials", Vol. 41, No. 1, p. 10 (1993)]. This fluorescent lamp admits air through a gap in the cover, allows the incoming air to contact the semiconductor, and frees the air of malodorous substances by decomposing the substances by the oxidizing and reducing actions of the electrons and positive holes produced in the semiconductor by the light from the fluorescent lamp.

With this device, however, flies, mosquitoes, moths and other small insects enter the interior of the fluorescent lamp through the gap formed in the cover, collect inside the cover, and eventually foul the inside of the cover to the point of blocking the incident light from passing through the cover. Thus, this device experiences a serious decline in its ability to remove malodorous substances by decomposition. To prevent this trouble, the interior of the cover of the fluorescent lamp must be cleaned frequently. Thus, there is a need to develop a deodorizing device which requires no cleaning after it has been installed and which retains its ability to decompose malodorous substances for a long time.

SUMMARY OF THE INVENTION

The present inventors continued a study with a view to developing a deodorizing device which meets this need. This invention has been accomplished as a result.

To be specific, the inventors found that a deodorizing lamp produced by coating the glass surface of the lamp with titanium oxide allows effective decomposition and removal of malodorous substances by virtue of oxidizing and reducing actions of the electrons and positive holes produced in the titanium oxide film by the light from within, requires no maintenance, and retains its ability to decompose malodorous substances for a long time. They further found that the ability of the deodorizing lamp to decompose malodorous substances is further enhanced by depositing on the titanium oxide film at least one metal selected from among iron, platinum, rhodium, ruthenium, palladium, silver, copper, zinc, and manganese. This knowledge was applied to further improve the invention.

DETAILED DESCRIPTION OF THE PREFERRED EMBODIMENT

Specifically, the present invention is directed to a deodorizing lamp comprising a lamp unit and a titanium oxide film coating the glass surface of the lamp unit, a deodorizing lamp comprising a lamp unit, a titanium oxide film coating the glass surface of the lamp unit, and at least one metal selected from among iron, platinum, rhodium, ruthenium, palladium, silver, copper, zinc, and manganese deposited on the titanium oxide film, and a method for the production of a deodorizing lamp by coating the glass surface of a lamp unit with a titania sol solution or an aqueous hydrogen peroxide solution of titania gel, then drying the applied layer of the solution, firing the dried layer thereby forming a titanium oxide film, and optionally depositing on the surface of the titanium oxide film at least one metal selected from among iron, platinum, rhodium, ruthenium, palladium, silver, copper, zinc, and manganese.

As concrete examples of the lamp unit to be used for the deodorizing lamp of this invention, an incandescent lamp, a fluorescent lamp, a black-light lamp, an ultraviolet (UV) lamp, a mercury-vapor lamp, a xenon flash lamp, a halogen lamp, and a metal halide lamp may be cited. The lamp may be cylindrical, bulbous, or of some complicated shape. For enhancing the effectiveness of the deodorizing lamp, the lamp unit is desired to produce light with a large shortwave light component.

The titanium oxide film which coats the glass surface of the lamp unit in this invention may be transparent or white. From the point of view of the durability of the film, however, the film is desired to be transparent.

Practically, the thickness of the titanium oxide film is desired to be in the range of 1 nm to 2 µm. If the thickness is unduly small, the ability of the deodorizing lamp to decompose malodorous substances and consequently its ability to deodorize the air is inferior. Conversely, if the thickness is unduly large, the ability of the lamp to illuminate is impaired, while its ability to deodorize the air does not increase proportionately to the increase in thickness.

The titanium oxide film used for this invention may be produced by the CVD (chemical vapor deposition) method or a PVD (physical vapaor deposition) method, including one that involves sputtering. It may be otherwise produced by coating the glass surface of a lamp unit with a suspension of a superfine titanium oxide powder by the dip coating method, the spin coating method, the brush coating method, the spray method, etc. and then firing the applied layer of the suspension. Preferably the film is produced by forming an alkoxide of titanium by the reaction of titanium tetrachloride or metallic titanium with an alcohol, preparing a titania sol solution from the alkoxide of titanium, coating the glass surface of the lamp unit with the titania sol solution by the dip coating method, the spin coating method, the brush coating method, or the spray method and the firing the applied layer of the solution. Instead of the titania sol solution, there can be used an aqueous hydrogen peroxide solution of titania gel obtained by drying titania sol. In any case, first a thin film of the solution mentioned above is uniformly formed on the glass surface of a lamp unit.

As concrete examples of the method which is effectively used for the formation of this thin film, the spreading method, the spray coating method, the spin coating method, and the dip coating method which pulls up the lamp unit at a low speed from the solution may be cited.

When the thin film of the solution consequently formed is fired, it gives rise to a $TiO_2$ film. A solid multilayer film adhering fast to the glass surface is obtained by repeating the work just described. In consequence of this operation, a porous titanium oxide film having a large thickness, enjoying high tenacity, and exhibiting a strong ability to decompose malodorous substances in the air and consequently to deodorize the air can be obtained.

As concrete examples of the method for depositing at least one metal selected from among iron, platinum, rhodium, ruthenium, palladium, silver, copper, zinc, and manganese on the surface of titanium oxide, photoelectrodeposition, the CVD method, and PVD methods such as sputtering and vacuum deposition may be cited. When the amount of the metal deposited is excessively large, the cost of the produced deodorizing lamp is unduly high and the light emitted from the lamp is unduly weak. The amount of this metal, therefore, is desired to be not more than 30% by weight based on the amount of titanium oxide.

Further, the deposition of the metal is desired to be carried out with the cap of the lamp unit and the periphery thereof thoroughly masked so that the film will not conduct electricity from the deodorizing lamp while it is in service.

In the present invention, the application of the titanium oxide film to the surface of the glass portion of the lamp unit and further the deposition of the metal selected from among iron, platinum, rhodium, ruthenium, palladium, silver, copper, zinc, and manganese on the titanium oxide film may be performed either before or after the lamp unit has been fabricated. To be specific, it is allowable either to form the titanium oxide film on the glass surface of the finished lamp and then optionally deposit the selected metal on the titanium oxide film or to form the titanium oxide film on the surface of the glass member of the lamp unit before the lamp is fabricated and then optionally deposit the selected metal on the titanium oxide film.

The layer or layers deposited on the glass surface and dried must be fired. The object of this firing resides in converting the layer or layers into a film which possesses a crystalline structure exhibiting a high ability to decompose malodorous substances in the air and consequently deodorize the air and which excels in durability. The firing temperature is in the range of 200° to 700° C. If this temperature is unduly low, the film exhibits an inferior ability to decompose malodorous substances and lacks durability. If the temperature is unduly high, the film acquires a crystalline structure with only a low ability to decompose malodorous substances.

The deodorizing lamp according to this invention effectively decomposes and removes malodorous substances in the air owing to the oxidizing and reducing actions of the electrons and positive holes which are generated in the titanium oxide film on the glass surface by the light emitted from the light source. Unlike the conventional deodorizing lamp which comprises a fluorescent lamp and a layer of semiconductor lining the cover of the fluorescent lamp and which admits insects into the interior of the cover and thus has the problem of the light being blocked by dead insects before reaching the titanium oxide film, the deodorizing lamp of this invention requires no maintenance and retains its high capacity to decompose malodorous substances for a long time. Then, owing to the deposition of metal selected from among iron, platinum, rhodium, ruthenium, palladium, silver, copper, zinc, and manganese on top of the titanium oxide film, the catalytic action which is consequently generated further enhances the deodorizing effect of the deodorizing lamp while, at the same time, the antibacterial and antifungal action of the metal effectively prevents growth of infections microbes. Even when no electric power is being supplied to the deodorizing lamp, the titanium oxide film generates electrons and positive holes on exposure to sunlight or light from any nearby electric lamp and the oxidizing and reducing actions of the electrons and positive holes decomposes and removes malodorous substances in the air.

The deodorizing lamp of this invention is also capable of decomposing tobacco smoke. It is therefore safe from having its luminance degraded by adherence of tobacco smoke particles. Further, since the titanium oxide film absorbs harmful ultraviolet light emitted from the light source, the light emitted by the deodorizing lamp of the present invention is, among its other characteristics, easy on the eyes and safe for the human body. The deodorizing lamp according to this invention can therefore be utilized as a room lamp with excellent characteristics. Besides, it finds utility in numerous applications such as a deodorizing lamp for refrigerators, a deodorizing lamp for automobiles, and a deodorizing and sterilizing lamp for kitchens and toilets, for example.

The titanium oxide which is used in this invention is a compound widely used in coating materials, cosmetic articles, and tooth powder. It excels in weatherability and durability and is nontoxic and safe. Thus, the deodorizing lamp contemplated by this invention excels in waterproofness, heat-resistance, lightfastness, weatherability, stability, and safety. Further, the method of this invention is simple in procedure and is capable of producing a deodorizing lamp of high quality excelling in durability and stability at a lost cost.

This invention will now be described more specifically with reference to working examples and comparative experiments.

EXAMPLE 1

A transparent sol solution was prepared by diluting 0.1 mol of titanium tetraisopropoxide with 100 ml of anhydrous ethanol and stirring the product of dilution and simultaneously adding 2.7 ml of 2N hydrochloric acid to the stirred solution. This sol solution was applied by dip coating to the surface of a 100 W incandescent lamp to coat the lamp with a titanium oxide film. More specifically, this coating was attained by immersing the 100 W incandescent lamp in the sol solution, pulling up the lamp from the sol solution, drying the applied layer of the sol solution on the lamp, and then firing the dried layer under a reduced pressure at 250° C. By performing this procedure ten times, a titanium oxide film about 1 μm in thickness was produced on the surface of the lamp. The deodorizing lamp thus obtained was tested for deodorizing effect by the following method. First, the produced deodorizing lamp was placed in a closed container having an inner volume of 36 liters, 80 ppm of trimethylamine was introduced into the container as a malodorous substance with the aid of a syringe, and the deodorizing lamp was turned on. After one hour's use of the deodorizing lamp in the container, the air in the closed container was analyzed by gas chromatography to determine the concentration of trimethylamine. The concentration was found to be 10 ppm.

COMPARATIVE EXPERIMENT 1

The procedure of Example 1 was repeated, except that the 100 W incandescent lamp was not coated with a titanium oxide film. The concentration of trimethylamine decreased only to 72 ppm.

EXAMPLE 2

A transparent sol solution was prepared by adding 125 ml of titanium tetraisopropoxide to 20 ml of isopropyl alcohol, adding the resultant solution dropwise to 750 ml of distilled water under constant stirring, adding 6 ml of 70% nitric acid to the resultant mixture, and maintaining the resultant solution at 80° C. for eight hours. This sol solution was applied by spraying to the surface of a 75 W mercury-arc lamp to form a titanium oxide coat on the lamp. To be specific, this film was obtained by uniformly spraying the sol solution onto the surface of the mercury-arc lamp, drying the applied layer of the sol solution, and then firing the dired layer in an oxygen atmosphere at 300° C. A titanium oxide film about 1.2 μm in thickness was produced on the mercury-arc lamp by performing the procedure 12 times. The glass part of the coated lamp, with the cap part thereof masked, was immersed in an aqueous ethanol solution containing potassium chloroplatinate at a concentration of 2 g/liter. The solution was kept stirred with a magnetic stirrer and the glass part immersed therein was meanwhile kept exposed to the light from a 100 W mercury-arc lamp for four hours to effect deposition of platinum on the surface of the titanium oxide film by the photoelectrodeposition process. The amount of platinum thus deposited was 5% by weight based on the amount of the titanium oxide film. The deodorizing lamp thus obtained was tested for deodorizing effect in a similar manner to that of in Example 1. The test was specifically carried out by first placing the deodorizing lamp in a closed containing having an inner volume of 36 liters, introducing 35 ppm of isovaleric acid as a malodorous substance with the smell of sweat into the container with the aid of a syringe, and keeping the deodorizing lamp turned on. After one hour's use of the deodorizing lamp in the container, the air in the closed container was analyzed for isovaleric acid concentration by gas chromatography. The concentration was found to be 1 ppm.

COMPARATIVE EXPERIMENT 2

The procedure of Example 2 was repeated, except that a commercially available 75 W mercury-arc lamp not coated with a titanium oxide film was used instead. The concentration of isovaleric acid decreased only to 28 ppm.

EXAMPLE 3

A transparent sol solution was prepared by adding 125 ml of titanium tetrabutoxide to 20 ml of t-butyl alcohol, adding the resultant solution dropwise to 750 ml of distilled water under constant stirring, adding 5 ml of 70% hydrochloric acid to the resultant solution, and then maintaining the solution at 90° C. for eight hours. This sol solution was applied with a brush to the surface of a 20 W fluorescent lamp and the applied layer of the sol solution was dried and then fired under a reduced pressure at 250° C. A titanium oxide film about 0.2 μm in thickness was produced on the surface of the fluorescent lamp by performing the procedure three times. The deodorizing lamp thus obtained was tested for deodorizing effect in a similar manner to that in Example 1. Specifically, the test was carried out by first placing the deodorizing lamp in a closed container having an inner volume of 60 liters, introducing 90 ppm of acetic acid as a malodorous substance into the container with the aid of a syringe, and keeping the deodorizing lamp on. After one hour's use of the deodorizing lamp in the closed container, the air in the closed container was analyzed for acetic acid concentration by gas chromatography. The concentration was found to be 12 ppm.

COMPARATIVE EXPERIMENT 3

The procedure of Example 3 was repeated, except that a commercially available 20 W fluorescent lamp not coated with a titanium oxide film was used instead. The concentration of acetic acid in the air decreased only to 78 ppm.

EXAMPLE 4

A transparent sol solution was prepared by adding 125 ml of titanium tetraethoxide to 20 ml of ethyl alcohol, adding the resultant solution dropwise to 750 ml of distilled water under constant stirring, adding 10 ml of 50% nitric acid to the resultant solution, and maintaining this solution at 75° C. for eight hours. By the same dip coating method as in Example 1, this transparent sol solution was applied to the surface of a 75 W halogen lamp to coat the lamp with 10 layers of titanium oxide film. To be specific, a titanium oxide film about 1 μm in thickness was produced on the surface of the halogen lamp by immersing the lamp in the sol solution, pulling up the lamp from the sol solution, drying the deposited layer of the sol solution, firing the dried layer under a reduced pressure at 250° C., and performing this procedure ten times. With the cap part of the produced lamp masked, copper was vacuum deposited on the surface of the titanium oxide film. The deodorizing lamp thus obtained was tested for the deodorizing effect in a similar manner to that in Example 1. To be specific, the test was carried out by first placing the deodorizing lamp in a closed container having an inner volume of 36 liters, injecting 150 ppm of acetaldehyde as a malodorous substance into the container with the aid of a syringe, and keeping the deodorizing lamp on. After one hour's use of the deodorizing lamp in the closed container, the air in the container was analyzed for acetaldehyde concentration by gas chromatography. The concentration was found to have decreased to 13 ppm.

COMPARATIVE EXPERIMENT 4

The procedure of Example 4 was repeated, except that a commercially available 75 W halogen lamp not coated with a titanium oxide film was used instead. The concentration of acetaldehyde decreased only to 122 ppm.

EXAMPLE 5

A titania gel was prepared by adding 150 ml of titanium tetraisopropoxide dropwise to 500 ml of distilled water under constant stirring, filtering the resultant solution, and drying the residue of filtration. A yellow solution was produced by dissolving 43 g of the titania gel in 200 ml of an aqueous 30% hydrogen peroxide solution. This solution was applied by spraying to the surface of a 10 W black-light lamp to coat the lamp with a titanium oxide film. A titanium oxide film about 0.6 μm in thickness was produced on the surface of the black-light lamp by first uniformly spraying the solution on the surface of the black-light lamp, drying the applied layer of the solution, firing the dried layer under a reduced pressure at 200° C., and performing this procedure five times. With the cap part of this lamp masked, zinc was vacuum deposited on the surface of the titanium oxide film to coat the lamp with zinc. The deodorizing lamp thus obtained was tested for deodorizing effect in a similar manner to that in Example 1. More specifically, this test was carried out by first placing the deodorizing lamp in a closed container having an inner volume of 36 liters, injecting 80 ppm of pyridine as a malodorous substance into the container with the aid of a syringe, and keeping the deodorizing lamp on. After one hour's use of the deodorizing lamp in the closed container, the air in the container was analyzed for pyridine concentration by gas chromatography. The concentration was found to be 5 ppm.

COMPARATIVE EXPERIMENT 5

The procedure of Example 5 was repeated, except that a commercially available 10 W black-light lamp not coated with a titanium oxide film was used instead. The pyridine concentration decreased to only 63 ppm.

EXAMPLE 6

A titania gel was obtained by allowing 200 ml of titanium tetraethoxide to stand at rest in steam and drying the resultant. A yellow solution was prepared by dissolving 73 g of the titania gel in 350 ml of an aqueous 30% hydrogen peroxide solution. This solution was applied to the bulb of a 30 W UV sterilizing lamp to coat the lamp with a titanium oxide film. A titanium oxide film about 1.3 µm in thickness was produced by first applying the solution to the bulb of the UV sterilizing lamp, drying the applied layer of the solution, firing the dried layer under a reduced pressure at 250° C., and performing this procedure ten times. The deodorizing lamp thus obtained was tested for deodorizing effect in a similar manner to that in Example 1. To be specific, this test was carried out by first placing the deodorizing lamp in a closed container having an inner volume of 400 liters, injecting 60 ppm of dimethylamine as a malodorous substance into the container with the aid of a syringe, and keeping the deodorizing lamp on. After one hour's use of the deodorizing lamp in the closed container, the air in the container was analyzed for dimethylamine concentration by gas chromatography. The concentration was 3 ppm.

COMPARATIVE EXPERIMENT 6

The procedure of Example 6 was repeated, except that a commercially available 30 W UV sterilization lamp not coated with a titanium oxide film was used instead. The concentration of dimethylamine decreased only to 50 ppm.

EXAMPLE 7

A titania gel was obtained by adding 100 ml of titanium tetraisopropoxide to 700 ml of distilled water under constant stirring and then drying the resultant mixture. A yellow solution was prepared by dissolving 29 g of the titania gel in 150 ml of an aqueous 30% hydrogen peroxide solution. This solution was applied to the surface of an 85 W metal halide lamp by the same dip coating method as in Example 1 to coat the lamp with a titanium oxide film. A titanium oxide film about 1.3 µm in thickness was produced on the surface of the lamp by immersing the metal halide lamp in the solution, pulling up the lamp from the solution, drying the applied layer of the solution, firing the dried layer under a reduced pressure at 250° C., and performing this procedure ten times. With the cap part of the produced deodorizing lamp masked, silver was deposited on the surface of the titanium oxide film by sputtering. The amount of the silver thus deposited was 10% by weight based on the amount of the titanium oxide film. The deodorizing lamp thus produced was tested for deodorizing effect in a similar manner to that in Example 1. Specifically, this test was carried out by first placing the deodorizing lamp in a closed container having an inner volume of 36 liters, injecting 60 ppm of dimethylamine as a malodorous substance into the container with the aid of a syringe, and keeping the deodorizing lamp on. After one hour's use of the deodorizing lamp in the closed container, the air in the container was analyzed for dimethylamine concentration by gas chromatography. The concentration was 3 ppm.

COMPARATIVE EXPERIMENT 7

The procedure of Example 7 was repeated, except that a commercially available 85 W metal halide lamp not coated with a titanium oxide film was used instead. The concentration of dimethylamine decreased only to 41 ppm.

EXAMPLES 8, 9, 10, 11, 12 AND 13

Deodorizing lamps were produced by repeating the procedure of Example 7, except that rhodium, ruthenium, palladium, iron, copper and manganese were respectively deposited in the place of silver on the surface of the titanium oxide film. These deodorizing lamps were tested for deodorizing effect in the same manner as in Example 7. The deodorizing effects were equal to that of the deodorizing lamp of Example 7.

Japanese Patent Application No. 5-115439 filed Apr. 19, 1993 is hereby incorporated by reference.

What is claimed is:

1. A deodorizing lamp comprising a lamp unit, and a first film comprising titanium oxide, coated on a glass surface of said lamp unit, wherein said lamp unit has a wattage of at most 100 W, and said first film has deposited thereon not more than 30% by weight, based on the amount of said titanium oxide, of a second metal film comprising at least one metal selected from the group consisting of iron, platinum, rhodium, ruthenium, palladium, silver, copper, zinc and manganese.

2. A deodorizing lamp according to claim 1, wherein said first film has a thickness in the range of 1 nm to 2 µm.

3. A deodorizing lamp according to claim 1, wherein said lamp unit is a member selected from the group consisting of an incandescent lamp, a fluorescent lamp, a black-light lamp, a UV lamp, a mercury-arc lamp, a xenon lamp, a halogen lamp, and a metal halide lamp.

4. A deodorizing lamp according to claim 1, wherein said first film has been fired at a temperature of 200°–700° C.

5. A deodorizing lamp according to claim 1, wherein said first film is transparent.

6. A deodorizing lamp according to claim 5, wherein said first film consists essentially of titanium oxide, and said first film has a thickness in the range of 1 nm to 2 µm.

7. A deodorizing lamp according to claim 6, wherein said first film is coated on an exterior glass surface of said lamp unit, and said first film consists of titanium oxide.

8. A deodorizing lamp according to claim 1, wherein said first film is produced by:

applying to the glass surface of said lamp unit at least one member selected from the group consisting of a titania sol solution and an aqueous hydrogen peroxide solution of a titania gel, thereby forming on the glass surface a layer, drying said layer, and firing the resulting layer at a temperature of 200°–700° C.

9. A deodorizing lamp according to claim 1, wherein said first film consists essentially of titanium oxide.

10. A deodorizing lamp according to claim 1, wherein said first film is coated on an exterior glass surface of said lamp unit.

11. A deodorizing lamp comprising a lamp unit and a first film comprising titanium oxide, coated on a glass surface of said lamp unit, wherein said lamp unit is a member selected from the group consisting of a fluorescent lamp, a black-light lamp, a UV lamp, a mercury-arc lamp, a xenon lamp, a halogen lamp and a metal halide lamp, and said first film has deposited thereon not more than 30% by weight, based on the amount of said titanium oxide, of a second metal film comprising at least one metal selected from the group consisting of iron, platinum, rhodium, ruthenium, palladium, silver, copper, zinc and manganese.

12. A deodorizing lamp according to claim 11, wherein said first film has a thickness in the range of 1 nm to 2 μm.

13. A deodorizing lamp according to claim 11, wherein said first film has been fired at a temperature of 200°–700° C.

14. A deodorizing lamp according to claim 11, wherein said first film is transparent.

15. A deodorizing lamp according to claim 14, wherein said first film consists essentially of titanium oxide, and said first film has a thickness in the range of 1 nm to 2 μm.

16. A deodorizing lamp according to claim 15, wherein said first film is coated on an exterior glass surface of said lamp unit, and said first film consists of titanium oxide.

17. A deodorizing lamp according to claim 11, wherein said first film is produced by:

applying to the glass surface of said lamp unit at least one member selected from the group consisting of a titania sol solution and an aqueous hydrogen peroxide solution of a titania gel, thereby forming on the glass surface a layer, drying said layer, and firing the resulting layer at a temperature of 200°–700° C.

18. A deodorizing lamp according to claim 11, wherein said first film consists essentially of titanium oxide.

19. A deodorizing lamp according to claim 11, wherein said first film is coated on an exterior glass surface of said lamp unit.

* * * * *